(12) United States Patent
Kashu et al.

(10) Patent No.: US 10,539,517 B2
(45) Date of Patent: Jan. 21, 2020

(54) CHECKING DEVICE AND CHECKING METHOD

(71) Applicant: Sumitomo Chemical Company, Limited, Tokyo (JP)

(72) Inventors: Koji Kashu, Niihama (JP); Yoshitaka Shinomiya, Daegu (KR); Daizaburo Yashiki, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/122,122

(22) Filed: Sep. 5, 2018

(65) Prior Publication Data

US 2019/0079030 A1    Mar. 14, 2019

(30) Foreign Application Priority Data

Sep. 8, 2017  (JP) ................................. 2017-173485
Aug. 27, 2018  (JP) ................................. 2018-158655

(51) Int. Cl.

| G01N 23/02 | (2006.01) |
|---|---|
| G01N 23/18 | (2018.01) |
| G01N 23/083 | (2018.01) |
| G01N 23/04 | (2018.01) |
| H04N 5/32 | (2006.01) |

(52) U.S. Cl.
CPC ............. *G01N 23/18* (2013.01); *G01N 23/04* (2013.01); *G01N 23/083* (2013.01); *H04N 5/32* (2013.01)

(58) Field of Classification Search
CPC .......... G10N 23/046; G01N 2223/652; G01N 23/18; G01N 23/04; G01N 23/083; G06T 3/4038; H04N 5/32
See application file for complete search history.

(56) References Cited

U.S. PATENT DOCUMENTS 8,165,265 B2 * 4/2012 Niwa ................... G06T 11/003
                                                                378/27
2016/0041110 A1   2/2016 Matoba et al.

FOREIGN PATENT DOCUMENTS

| EP | 0166567 A2 | 1/1986 | |
|---|---|---|---|
| JP | 61-22841 A | 1/1986 | |
| JP | 3717491 B2 * | 11/2005 | ............. G01N 23/04 |
| JP | 2014020910 A | 2/2014 | |
| JP | 2016-38350 A | 3/2016 | |

* cited by examiner

*Primary Examiner* — Kiho Kim
(74) *Attorney, Agent, or Firm* — Panitch Schwarze Belisario & Nadel LLP

(57) ABSTRACT

The present invention makes it possible to check a target object highly accurately and quickly. In a sensor having an electromagnetic wave reception region, suitability of portions for capturing an image of a subject which moves fast is heightened as a distance from a center increases in a plan view of a circular profile surface.

10 Claims, 7 Drawing Sheets

CHECKING DEVICE AND CHECKING METHOD

This Nonprovisional application claims priority under U.S.C. § 119 on Patent Application No. 2017-173485 filed in Japan on Sep. 8, 2017 and Patent Application No. 2018-158655 filed in Japan on Aug. 27, 2018, the entire contents of which is hereby incorporated by reference.

TECHNICAL FIELD

The present invention relates to a checking device and a checking method.

BACKGROUND ART

Nonaqueous electrolyte secondary batteries such as a lithium-ion secondary battery are in wide use as batteries for devices such as a personal computer, a mobile telephone, and a portable information terminal. Among those, attention is being given to the lithium-ion secondary battery as a battery that reduces carbon dioxide emissions and contributes to energy saving, as compared with conventional secondary batteries.

Conventionally, separator rolls in each of which a nonaqueous electrolyte secondary battery separator is wound around a core have been developed. In addition, studies are being carried out in regard to checking for detecting foreign substances adhering to the separator roll.

As an example of check for detecting foreign substances adhering to a target object, a technique is disclosed in Patent Literature 1. In the technique disclosed in Patent Literature 1, an X-ray emitted from an X-ray source is converted into parallel X-rays by a capillary lens, then a sample which is a target object is irradiated with the parallel X-rays, and then a time delay integration (TDI) sensor receives the parallel X-rays which have passed through the sample. The TDI sensor employs, for example, a technique disclosed in Patent Literature 2.

In a case of detecting foreign substances adhering to a target object having a surface whose profile is a circle (e.g., a lateral surface of a separator roll), the following checking method may be employed. Note that, hereinafter, the surface of the target object whose profile is a circle is also referred to as "circular profile surface".

That is, the target object is rotated about an axis that (i) passes through a center of a circle constituting a profile of the circular profile surface and (ii) extends in a direction substantially perpendicular to the circular profile surface. Then, the circular profile surface is irradiated with an electromagnetic wave. Then, a sensor receives the electromagnetic wave which has passed through the circular profile surface. Then, images obtained when the sensor has received the electromagnetic wave are analyzed, and thus whether foreign substances are adhering to the target object or not is checked. From this, the detection of foreign substances can be carried out highly efficiently, and this makes it possible to enhance a speed of the check, as compared with the technique disclosed in Patent Literature 1.

CITATION LIST

Patent Literature

Patent Literature 1: Japanese Patent Application Publication Tokukai No. 2016-38350 (Publication Date: Mar. 22, 2016)

Patent Literature 2: Japanese Patent Application Publication Tokukaisho No. 61-22841 (Publication Date: Jan. 31, 1986)

SUMMARY OF INVENTION

Technical Problem

Here, in a case where the target object is rotated, a speed becomes higher as a distance from the center of the circle increases in a plan view of the circular profile surface. From this, in the above described check that is carried out by rotating the target object, for example, the following problems (A) and (B) occur in a case where obtainment of images in the vicinity of the center of the circle is optimized:

(A) An area of a portion of the circular profile surface, which portion is shown in an image obtained by the sensor, becomes larger in a rotation direction, as the distance from the center of the circle increases (in other words, the portion extends in the rotation direction). From this, resolution may be deteriorated and a blur may occur in an image at a location away from the center of circle, and/or the image at the location away from the center of circle may be misaligned relative to an image (whose resolution is not deteriorated) in the vicinity of the center of circle.

(B) This case assumes that a plurality of image capturing units (e.g., pixels) in an electromagnetic wave reception region of the sensor are arranged in a matrix manner constituted by rows along one certain radius of the circular profile surface and columns which are substantially perpendicular to the rows. In this case, misalignment of portions of the circular profile surface which are shown in obtained images (i.e., misalignment of those portions between image capturing units) becomes larger as the distance from the center of circle to the columns of image capturing units increases. For example, in a case where the sensor is a TDI sensor, images which have been obtained by respective image capturing units constituting a certain column of image capturing units are to be superimposed. In such a case, the misalignment leads to a blur in an image obtained by the superimposition.

That is, in the above described check which is carried out while the target object is rotated, it is difficult to obtain a clear image of the entire circular profile surface, and a problem of low accuracy in the check occurs.

An object of an aspect of the present invention is to provide a checking device and a checking method which make it possible to check a target object highly accurately and quickly.

Solution to Problem

In order to attain the object, a checking device in accordance with an aspect of the present invention is a checking device for checking a target object having a circular profile surface, which is a surface whose profile is a circle, while rotating the target object about an axis that passes through a center of the circle and extends in a direction substantially perpendicular to the circular profile surface, the checking device including: at least one electromagnetic wave source which irradiates the circular profile surface of the target object, which is being checked, with an electromagnetic wave; and an image capturing section which has an electromagnetic wave reception region for receiving the electromagnetic wave which has passed through the target object which is being checked, in the image capturing section, suitability of portions of the electromagnetic wave reception region for capturing an image of a subject which moves fast being heightened as a distance from the center of the circle increases in a plan view of the circular profile surface of the target object which is being checked.

Moreover, in order to attain the object, a checking method in accordance with an aspect of the present invention is a checking method for checking a target object having a circular profile surface, which is a surface whose profile is a circle, while rotating the target object about an axis that passes through a center of the circle and extends in a direction substantially perpendicular to the circular profile surface, the checking method including the steps of: irradiating the circular profile surface of the target object, which is being checked, with an electromagnetic wave; and receiving, by an electromagnetic wave reception region included in an image capturing section, the electromagnetic wave which has passed through the target object which is being checked, in the image capturing section, suitability of portions of the electromagnetic wave reception region for capturing an image of a subject which moves fast being heightened as a distance from the center of the circle increases in a plan view of the circular profile surface of the target object which is being checked.

Advantageous Effects of Invention

According to an aspect of the present invention, it is possible to enhance accuracy and a speed in checking a target object.

DESCRIPTION OF EMBODIMENTS

The following description will discuss embodiments of the present invention with reference to FIGS. 1 through 10.

Figure 1:
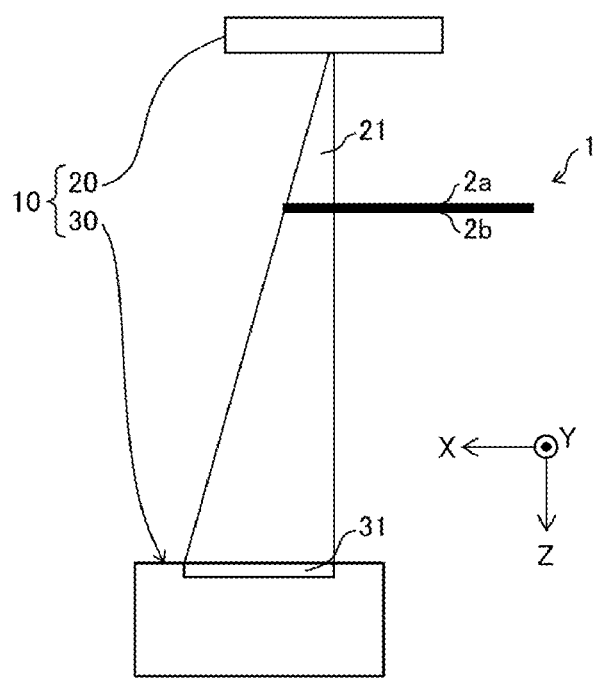
FIG. 1 is a schematic view illustrating a checking device in accordance with Embodiment 1 and Embodiment 2 of the present invention.

FIG. 1 is a schematic view illustrating a checking device 10 in accordance with Embodiment 1 and Embodiment 2 of the present invention. The checking device 10 checks a target object 1, specifically, checks presence or absence of a foreign substance that adheres to the target object 1. The checking device 10 includes an electromagnetic wave source 20 and a sensor (image capturing section) 30.

The target object 1 has a circular profile surface $2a$ and a circular profile surface $2b$ each of which is a surface whose profile is a circle. In FIG. 1, the circular profile surface $2a$ is located on an electromagnetic wave source 20 side, and the circular profile surface $2b$ is located on a sensor 30 side. A shape of the target object 1 can be a doughnut shape, a disc shape, a cylindrical shape, a columnar shape, or the like. Specific examples of the target object 1 encompass a separator roll in which a nonaqueous electrolyte secondary battery separator is wound around a core, a core around which a nonaqueous electrolyte secondary battery separator is wound, and the like.

Figure 2:
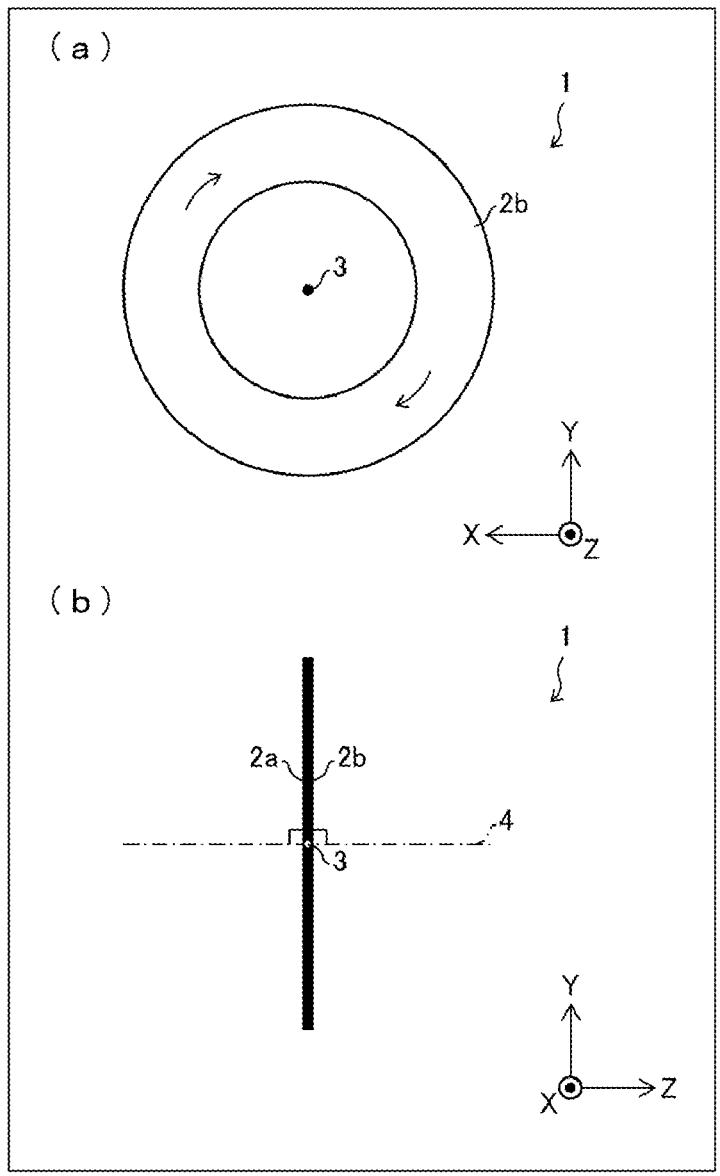
FIG. 2 is a view illustrating a state in which a target object is rotated, where (a) of FIG. 2 is a plan view of a circular profile surface, and (b) of FIG. 2 shows a lateral view of the target object.

FIG. 2 is a view illustrating a state in which the target object 1 is rotated. (a) of FIG. 2 is a plan view of the circular profile surface $2b$. (b) of FIG. 2 shows a lateral view of the target object 1. Specifically, (b) of FIG. 2 illustrates a state in which the electromagnetic wave source 20 side is on the left, and the sensor 30 side is on the right.

Note that, in each of the embodiments, three directions (i.e., X direction, Y direction, and Z direction) are defined which are perpendicular to each other. The X direction is a width direction of the target object 1, the Y direction is a height direction of the target object 1, and the Z direction is a direction which is perpendicular to both the X direction and the Y direction and perpendicularly passes through the circular profile surface $2a$ and the circular profile surface $2b$.

In a state in which the target object 1 is checked by the checking device 10, the target object 1 is rotated about an axis 4 that (i) passes through a center 3 of a circle constituting a profile of the circular profile surface $2b$ and (ii) extends in a direction (Z direction) substantially perpendicular to the circular profile surface $2b$. A similar relation holds true also between the target object 1 and the circular profile surface $2a$. A rotation direction is a clockwise direction in the plan view of the circular profile surface $2b$. However, the rotation direction can be an anticlockwise direction in the plan view of the circular profile surface $2b$.

The electromagnetic wave source 20 irradiates the circular profile surface $2a$ with an electromagnetic wave 21. The electromagnetic wave 21 can be, for example, an X-ray. The electromagnetic wave 21 which has been emitted from the electromagnetic wave source 20 toward the circular profile surface 2a passes through the target object 1 and then exits through the circular profile surface 2b.

The sensor 30 can be, for example, a TDI sensor, and has an electromagnetic wave reception region 31. The electromagnetic wave reception region 31 includes a plurality of pixels, and the plurality of pixels receive the electromagnetic wave 21 which has passed through the target object 1. The electromagnetic wave reception region 31 can be provided with at least one lens which covers the plurality of pixels. The sensor 30 receives the electromagnetic wave 21 on the electromagnetic wave reception region 31, and thus obtains an image of a portion in the circular profile surface 2a and in the circular profile surface 2b through which portion the electromagnetic wave 21 has passed.

In Embodiment 1 and Embodiment 2 below, electromagnetic wave reception regions 31a through 31c will be described each of which is a concrete example configuration of the electromagnetic wave reception region 31.

Embodiment 1

Figure 3:
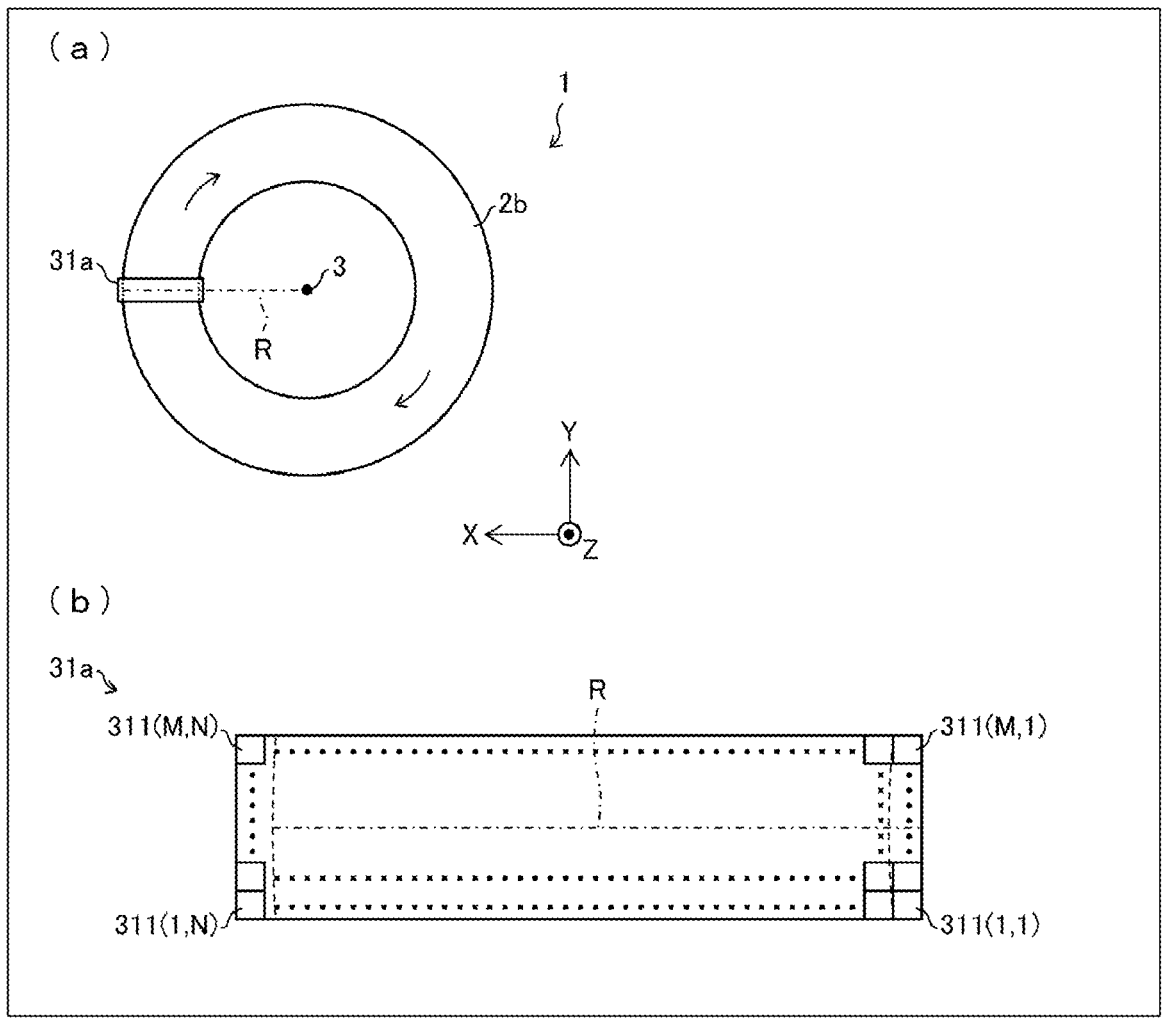
FIG. 3 is a view illustrating a configuration of an electromagnetic wave reception region in accordance with Embodiment 1 of the present invention, where each of (a) and (b) of FIG. 3 is a plan view of the circular profile surface.

Each of (a) and (b) of FIG. 3 is a plan view of the circular profile surface 2b and illustrates a configuration of an electromagnetic wave reception region 31a in accordance with Embodiment 1. In (a) of FIG. 3, in order to simplify the drawing, constituent members other than the circular profile surface 2b, the center 3, and the electromagnetic wave reception region 31a are not illustrated. (b) of FIG. 3 is an enlarged view illustrating only the electromagnetic wave reception region 31a shown in (a) of FIG. 3.

In the plan view of the circular profile surface 2b, the electromagnetic wave reception region 31a is arranged such that a whole of the circular profile surface 2b overlaps with the electromagnetic wave reception region 31a when the target object 1 is rotated once in a manner illustrated in FIG. 2. The electromagnetic wave reception region 31a includes a plurality of pixels 311. The plurality of pixels 311 are arranged in a matrix of M rows×N columns. Each of the M rows extends along a radius R of the circular profile surface 2b, and each of the N columns is substantially perpendicular to each of the M rows.

In (a) and (b) of FIG. 3, an order of the M rows (like first row, second row, . . . M-th row) starts from an uppermost stream side of the rotation of the target object 1. Moreover, in (a) and (b) of FIG. 3, an order of the N columns (like first column, second column, . . . N-th column) starts from a side that is nearer to the center 3. In (a) and (b) of FIG. 3, a pixel 311 which is located at an m-th (1≤m≤M) row and an n-th (1≤n≤N) column is indicated as a pixel 311(m,n).

Here, in the plan view of the circular profile surface 2b, the electromagnetic wave reception region 31a is configured such that suitability of portions of the electromagnetic wave reception region 31a for capturing an image of a subject which moves fast is heightened as a distance from the center 3 increases. Here, "suitability for capturing an image of a subject which moves fast" means that performance of a corresponding sensor 30 is secured to an extent that a clear image without a blur can be obtained when an image of the subject which moves fast is captured. In other words, in a case where the pixels 311 are arranged in an ascending order of suitability with respect to image-capture of the subject which moves fast, the first column is constituted by pixels 311(1,1) through 311(M,1), the second column is constituted by pixels 311(1,2) through 311(M,2), . . . and the N-th column is constituted by pixels 311(1,N) through 311(M,N).

As a method for heightening suitability with respect to capturing an image of a subject which moves fast, the following configuration (1) or (2) may be applied to the sensor 30 or a device (image capturing section) provided around the sensor 30, in relation to the plurality of pixels 311 and a plurality of imaging mechanisms (not illustrated) corresponding to the respective plurality of pixels 311. Note that the configurations (1) and (2) can be achieved by known techniques, and therefore details of those configurations are not described here.

(1) Increase a shutter speed in capturing an image.

(2) While capturing images in an order from the first row (i.e., pixels 311(1,1) through 311(1,N)), then the second row (i.e., pixels 311(2,1) through 311(2,N)), . . . , to the M-th row (i.e., pixels 311(M,1) through 311(M,N)), the number of sequentially-captured images increases for columns with higher suitability with respect to capturing of an image of a subject which moves fast.

According to the configuration, suitability of portions of the electromagnetic wave reception region 31a of the image capturing section for capturing an image of a subject which moves fast is heightened as a distance from the center 3 increases in the plan view of the circular profile surface 2b. With the configuration, it is possible to inhibit an area of a portion of the circular profile surface 2b, which portion is shown in an image obtained in the electromagnetic wave reception region 31a, from becoming larger in a rotation direction at a location which is away from the center 3, and this makes it possible to inhibit the above described problem (A).

Moreover, according to the configuration, it is possible to inhibit misalignment of portions of the circular profile surface 2b, shown in obtained images, between pixels 311 which constitute the same column in the electromagnetic wave reception region 31a. Therefore, it is possible to inhibit the above described problem (B).

As such, according to the configuration, it is possible to check the target object 1 highly accurately and quickly.

Further, in the configuration (2), images obtained by the respective pixels 311 can be evenly reduced as appropriate such that a particular location in the circular profile surface 2b is always shown around a center of an image. From this, it is possible to further inhibit the above described problem (B).

Figure 4:
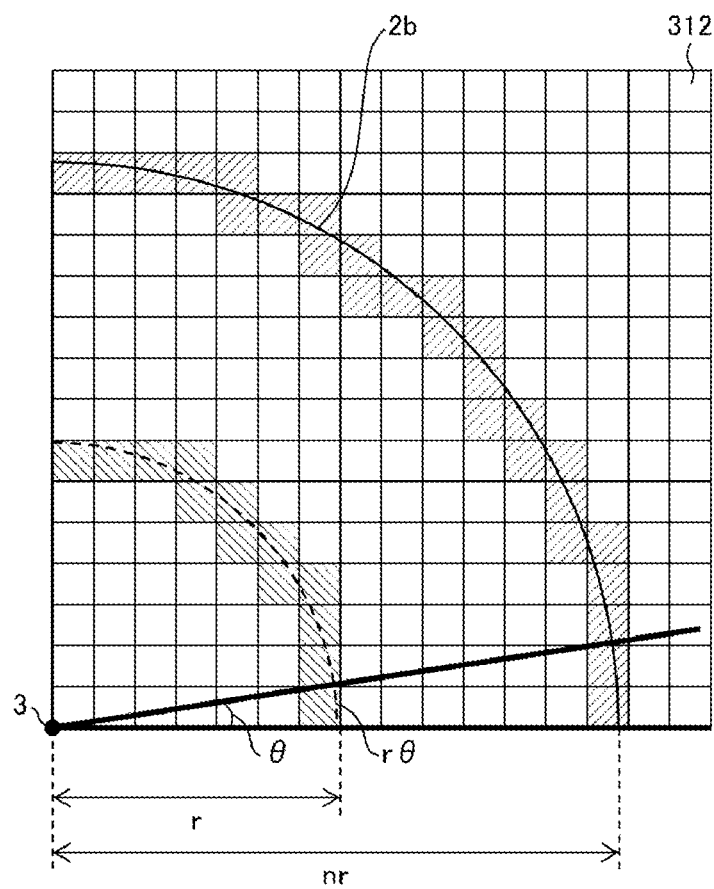
FIG. 4 is a view for explaining an effect of inhibiting a problem that misalignment of portions of the circular profile surface which are shown in obtained images (i.e., misalignment of those portions between image capturing units) becomes larger as the distance from the center of circle to columns of image capturing units increases.

The following description will discuss further details of an effect of inhibiting the above described problem (B) with reference to FIGS. 4 through 7. Each of FIGS. 4 through 7 is a view for explaining the effect of inhibiting the above described problem (B). In FIG. 4, an explanation is made with reference to an image of the circular profile surface 2b and images in the plurality of pixels 312.

In a case where a size of each of the pixels 312 is sufficiently small, the number of pixels 312 for obtaining images of a circumference of a circle whose center is the axis 4 (i.e., the number of pixels 312 which overlap with the circumference of the circle in the plan view of the circular profile surface 2b) is approximately proportional to a radius of the circle.

In a case where the number of pixels 312 for obtaining images of a circumference of a circle having a radius r is $2\pi r$ pieces, the number of pixels 312 for obtaining images of a circumference of a circle having a radius nr (1<n) is $2\pi nr$ pieces.

With reference to FIG. 4, in a case where a central angle constituted by two radii, which circumscribe one of pixels 312 for obtaining images of the circumference of the circle with the radius r, is $\theta$, a size of one pixel 312 is $r\theta$. From this, the number of pixels 312 for obtaining images of the circumference of the circle with the radius r is $2\pi r/r\theta = 2\pi/\theta$ pieces. In a case where the size of each of pixels 312 for obtaining images of the circumference of the circle with the radius nr is rθ, the number of pixels 312 for obtaining images of the circumference of the circle with the radius nr is 2πnr/rθ=2πn/θ pieces.

Figure 5:
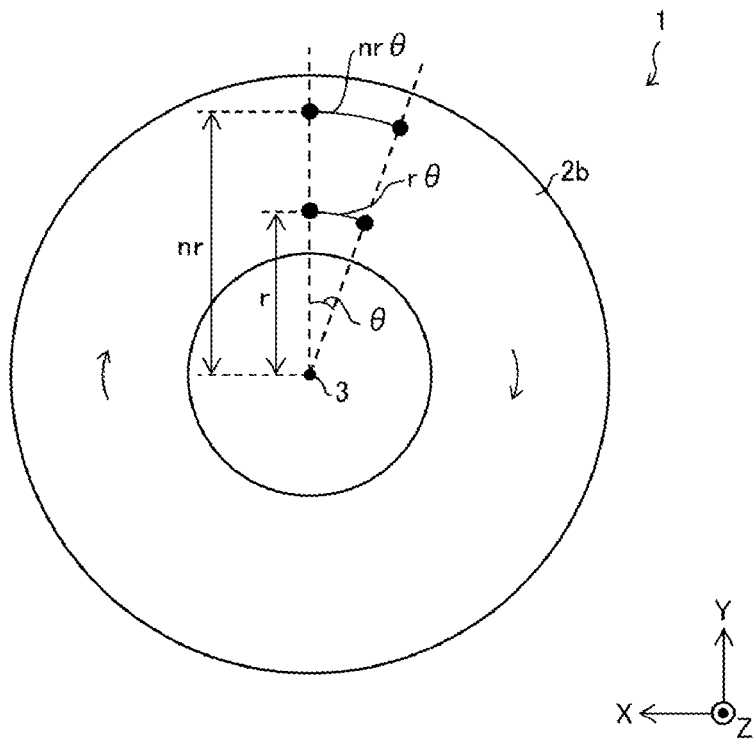
FIG. 5 is a view for explaining an effect of inhibiting a problem that misalignment of portions of the circular profile surface which are shown in obtained images (i.e., misalignment of those portions between image capturing units) becomes larger as the distance from the center of circle to columns of image capturing units increases.
Figure 6:
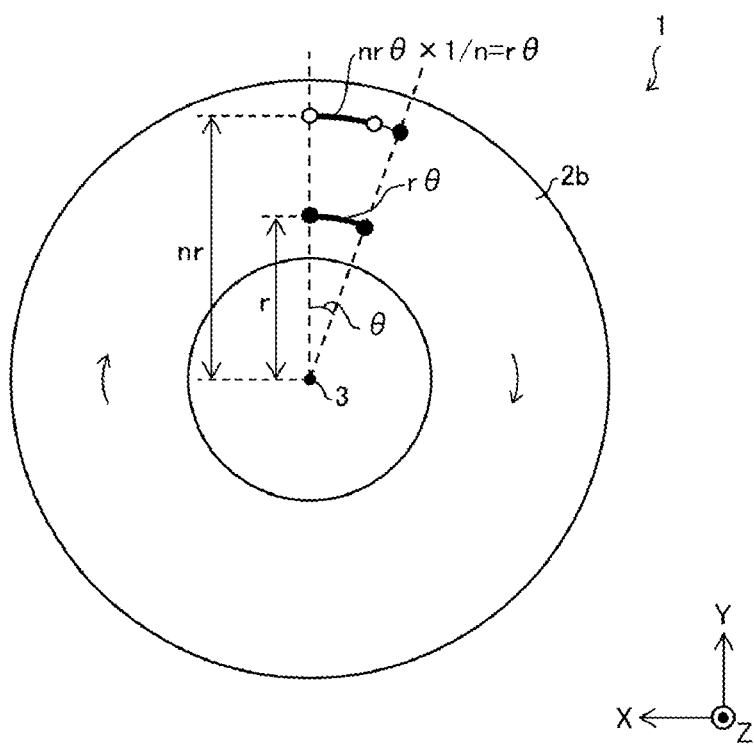
FIG. 6 is a view for explaining an effect of inhibiting a problem that misalignment of portions of the circular profile surface which are shown in obtained images (i.e., misalignment of those portions between image capturing units) becomes larger as the distance from the center of circle to columns of image capturing units increases.
Figure 7:
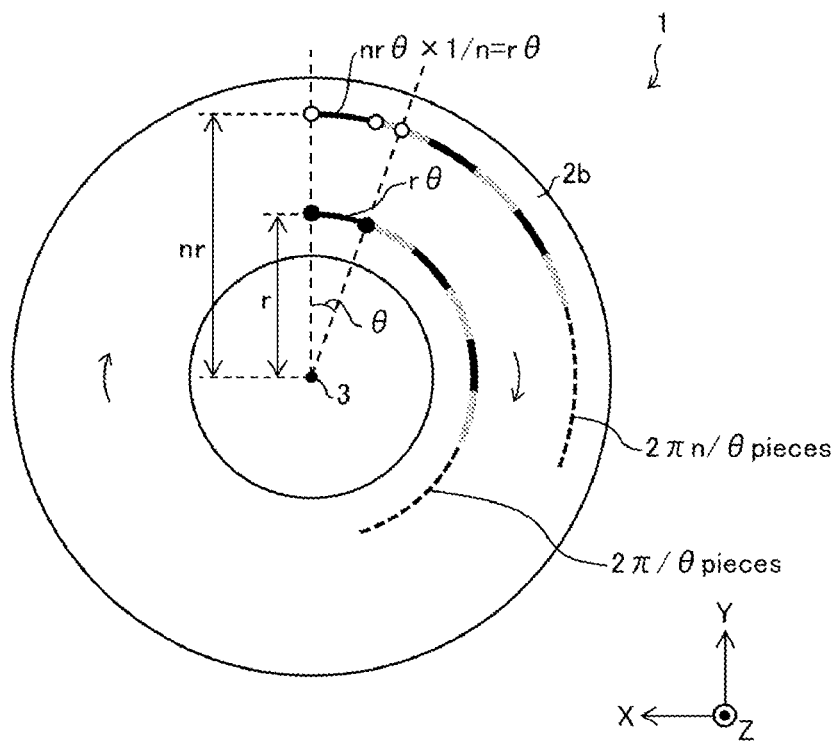
FIG. 7 is a view for explaining an effect of inhibiting a problem that misalignment of portions of the circular profile surface which are shown in obtained images (i.e., misalignment of those portions between image capturing units) becomes larger as the distance from the center of circle to columns of image capturing units increases.

Here, as illustrated in FIG. 5, in a case where an image of the circular profile surface 2b is obtained, a moving speed in rotation of the target object 1 increases, as a distance from the center 3 increases. Therefore, in a case where an image on the circumference of the circle with the radius r and an image on the circumference of the circle with the radius nr are obtained by taking the same time, a moving distance per image obtained is longer on the circumference of the circle with the radius nr. In order to cancel the difference in moving distance, it is effective to set a shutter time of an imaging mechanism, which corresponds to each of the pixels 312 for obtaining images of the circumference of the circle with the radius nr, to be 1/n times a shutter time of an imaging mechanism corresponding to each of the pixels 312 for obtaining images of the circumference of the circle with the radius r (see FIG. 6 and FIG. 7). In a case where the shutter time is 1/n times, this means that a shutter speed is n times. In a case where the sensor 30 is a TDI sensor, 2π/θ pieces of data are added up for the pixels 312 for obtaining images of the circumference of the circle with the radius r, while 2πn/θ pieces of data can be added up for the pixels 312 for obtaining images of the circumference of the circle with the radius nr.

Figure 8:
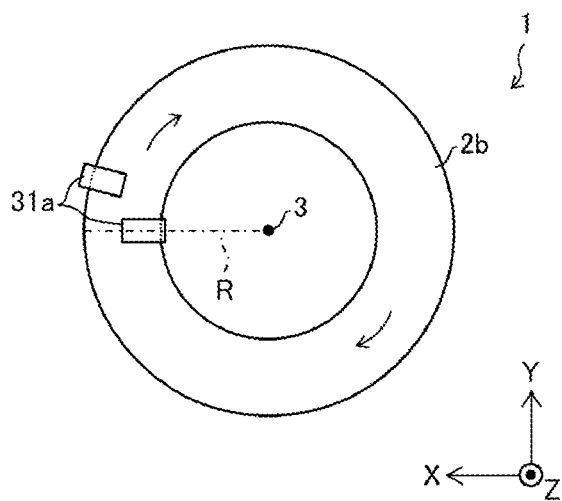
FIG. 8 is a plan view of the circular profile surface and illustrates a configuration of a modification example of the electromagnetic wave reception region illustrated in (a) of FIG. 3.

FIG. 8 is a plan view of the circular profile surface 2b and illustrates a configuration of a modification example of the electromagnetic wave reception region 31a. In the modification example, a part of the electromagnetic wave reception region 31a is arranged by being shifted along the moving direction of the circular profile surface 2b in the rotation of the target object 1, as compared with the arrangement illustrated in (a) of FIG. 3. In other words, in this modification example, at least one of the plurality of pixels 311 in the electromagnetic wave reception region 31a is located away from the other pixels 311.

Embodiment 2

Figure 9:
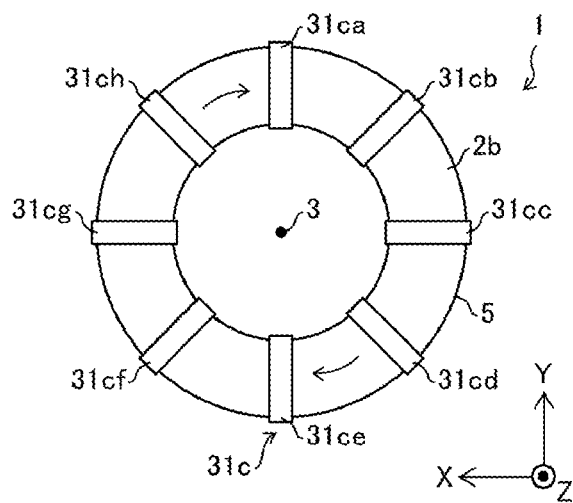
FIG. 9 is a plan view of the circular profile surface and illustrates a configuration of an electromagnetic wave reception region in accordance with Embodiment 2 of the present invention.

FIG. 9 is a view illustrating a configuration of an electromagnetic wave reception region 31c in accordance with Embodiment 2, and is a plan view of the circular profile surface 2b. In FIG. 9, in order to simplify the drawing, constituent members other than the circular profile surface 2b, the center 3, and the electromagnetic wave reception region 31c are not illustrated.

The electromagnetic wave reception region 31c is divided into a plurality of smaller regions (in FIG. 9, eight smaller regions, i.e., smaller regions 31c through 31ch). Each of the smaller regions 31ca through 31ch has a configuration similar to the electromagnetic wave reception region 31a (see (a) and (b) of FIG. 3). Further, the smaller regions 31ca through 31ch are arranged concentrically with a circumference 5 of the circular profile surface 2b.

According to the configuration, it is possible to receive, at each of the smaller regions 31ca through 31ch, the electromagnetic wave 21 which passes through a particular portion in the circular profile surface 2b, and this makes it possible to increase types of data to be used in the check.

The checking device 10 having the plurality of smaller regions 31ca through 31ch as the electromagnetic wave reception region 31 preferably has the following configuration. That is, the smaller regions 31ca through 31ch receive the electromagnetic wave 21 from the same portion of the circular profile surface 2b at respectively different points in time. Then, the checking device 10 checks presence or absence of a foreign substance adhering to the same portion by superimposing a plurality of images of the same portion which have been obtained when the smaller regions 31ca through 31ch receive the electromagnetic wave 21.

According to the configuration, it is possible to improve accuracy of the check by superimposing a plurality of images of the same portion while utilizing a principle of the TDI sensor.

Embodiment 3

Figure 10:
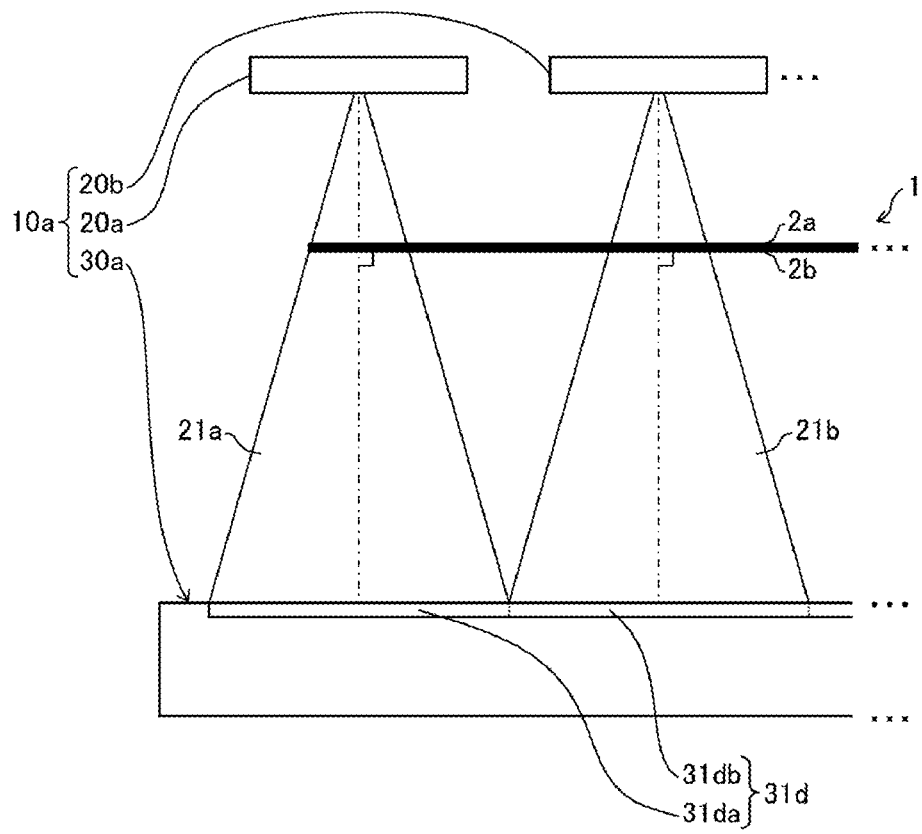
FIG. 10 is a schematic view illustrating a checking device in accordance with Embodiment 3 of the present invention.

FIG. 10 is a schematic view illustrating a checking device 10a in accordance with Embodiment 3 of the present invention. The checking device 10a is different from the checking device 10 in that the checking device 10a includes a plurality of electromagnetic wave sources 20a, 20b, and so forth instead of the electromagnetic wave source 20, and includes a sensor 30a instead of the sensor 30.

The sensor 30a is different from the sensor 30 in that the sensor 30a includes an electromagnetic wave reception region 31d instead of the electromagnetic wave reception region 31. The electromagnetic wave reception region 31d is constituted by a plurality of image capturing units (e.g., a plurality of pixels) 31da, 31db, and so forth. The image capturing units 31da, 31db, and so forth correspond to the electromagnetic wave sources 20a, 20b, and so forth, respectively. Each of the electromagnetic wave sources 20a, 20b, and so forth is provided such that a direction from each of the electromagnetic wave sources 20a, 20b, and so forth to a corresponding one of the image capturing units 31da, 31db, and so forth is substantially perpendicular to the circular profile surface 2b. That is, the electromagnetic wave sources 20a, 20b, and so forth emit electromagnetic waves 21a, 21b, and so forth, respectively, and the electromagnetic waves 21a, 21b, and so forth pass through the target object 1. The image capturing units 31da, 31db, and so forth respectively receive the electromagnetic waves 21a, 21b, and so forth which have passed through the target object 1.

Alternatively, instead of the configuration of the checking device 10a, it is possible that the number of electromagnetic wave sources 20a, 20b, and so forth can be smaller than the number of image capturing units 31da, 31db, and so forth.

With regard to the smaller regions 31ca through 31ch illustrated in FIG. 9, it is possible that each of the plurality of electromagnetic wave sources is provided such that a direction from each of the plurality of electromagnetic wave sources to a corresponding one of the smaller regions 31ca through 31ch is substantially perpendicular to the circular profile surface 2b, as with the configuration illustrated in FIG. 10. Alternatively, instead of this configuration, it is possible that the number of electromagnetic wave sources is smaller than the number of smaller regions 31ca through 31ch.

[Additional Remarks]

Note that, in the check, it is not essential to use the checking device 10, and a checking method in which operations similar to those of the checking device 10 are carried out is also encompassed within the scope of the present invention.

[Recap]

The checking device in accordance with an aspect of the present invention is a checking device for checking a target object having a circular profile surface, which is a surface whose profile is a circle, while rotating the target object about an axis that passes through a center of the circle and extends in a direction substantially perpendicular to the circular profile surface, the checking device including: at least one electromagnetic wave source which irradiates the circular profile surface of the target object, which is being checked, with an electromagnetic wave; and an image capturing section which has an electromagnetic wave reception region for receiving the electromagnetic wave which has passed through the target object which is being checked, in the image capturing section, suitability of portions of the electromagnetic wave reception region for capturing an image of a subject which moves fast being heightened as a distance from the center of the circle increases in a plan view of the circular profile surface of the target object which is being checked.

Moreover, the checking method in accordance with an aspect of the present invention is a checking method for checking a target object having a circular profile surface, which is a surface whose profile is a circle, while rotating the target object about an axis that passes through a center of the circle and extends in a direction substantially perpendicular to the circular profile surface, the checking method including the steps of: irradiating the circular profile surface of the target object, which is being checked, with an electromagnetic wave; and receiving, by an electromagnetic wave reception region included in an image capturing section, the electromagnetic wave which has passed through the target object which is being checked, in the image capturing section, suitability of portions of the electromagnetic wave reception region for capturing an image of a subject which moves fast being heightened as a distance from the center of the circle increases in a plan view of the circular profile surface of the target object which is being checked.

According to the configuration, in a plan view of the round outer surface, suitability of portions of the electromagnetic wave reception region for capturing an image of a subject which moves fast is heightened as a distance from the center of the circle constituting the profile of the circular profile surface increases. With the configuration, it is possible to inhibit an area of a portion of the circular profile surface, which portion is shown in an image obtained by the image capturing section, from becoming larger in a rotation direction at a location which is away from the center of the circle, and this makes it possible to inhibit the above described problem (A).

Moreover, according to the configuration, it is possible to inhibit misalignment of portions of the circular profile surface, shown in obtained images, between image capturing units which constitute the same column in the electromagnetic wave reception region. Therefore, it is possible to inhibit the above described problem (B).

As such, according to the configuration, it is possible to check a target object highly accurately and quickly.

In the checking device in accordance with an aspect of the present invention, the electromagnetic wave reception region is divided into a plurality of smaller regions and, in the plan view of the circular profile surface, the plurality of smaller regions are arranged concentrically with a circumference of the circular profile surface.

In the checking method in accordance with an aspect of the present invention, the electromagnetic wave reception region is divided into a plurality of smaller regions and, in the plan view of the circular profile surface, the plurality of smaller regions are arranged concentrically with a circumference of the circular profile surface.

According to the configuration, it is possible to receive, at each of the smaller regions, the electromagnetic wave which passes through a particular portion in the circular profile surface, and this makes it possible to increase types of data to be used in the check.

In the checking device in accordance with an aspect of the present invention, the plurality of smaller regions receive the electromagnetic wave, which passes through a certain portion of the circular profile surface, at respectively different points in time; and the checking device checks presence or absence of a foreign substance adhering to the certain portion by superimposing a plurality of images of the certain portion which have been obtained when the plurality of smaller regions receive the electromagnetic wave.

In the checking method in accordance with an aspect of the present invention, the plurality of smaller regions receive the electromagnetic wave, which passes through a certain portion of the circular profile surface, at respectively different points in time and, in the checking method, presence or absence of a foreign substance adhering to the certain portion is checked by superimposing a plurality of images of the certain portion which have been obtained when the plurality of smaller regions receive the electromagnetic wave.

According to the configuration, it is possible to improve accuracy of the check by superimposing a plurality of images of the same portion while utilizing a principle of the TDI sensor.

In the checking device in accordance with an aspect of the present invention, it is possible that the at least one electromagnetic wave source of the checking device is a plurality of electromagnetic wave sources which are associated with the respective plurality of smaller regions; and each of the plurality of electromagnetic wave sources is provided such that a direction from each of the plurality of electromagnetic wave sources to a corresponding one of the plurality of smaller regions is substantially perpendicular to the circular profile surface.

In the checking method in accordance with an aspect of the present invention, it is possible that the electromagnetic wave is generated in a direction substantially perpendicular to the circular profile surface for each of the plurality of smaller regions.

According to the configuration, it is possible to uniformize traveling directions of electromagnetic waves toward the respective smaller regions. From this, it is possible to inhibit misalignment, which may be caused depending on a thickness or the like of the target object, between images obtained by the respective smaller regions.

In the checking device in accordance with an aspect of the present invention, it is possible that the electromagnetic wave reception region is constituted by a plurality of image capturing units; the at least one electromagnetic wave source of the checking device is a plurality of electromagnetic wave sources which are associated with the respective plurality of image capturing units; and each of the plurality of electromagnetic wave sources is provided such that a direction from each of the plurality of electromagnetic wave sources to a corresponding one of the plurality of image capturing units is substantially perpendicular to the circular profile surface.

In the checking method in accordance with an aspect of the present invention, it is possible that the electromagnetic wave reception region is constituted by a plurality of image capturing units; and the electromagnetic wave is generated in a direction substantially perpendicular to the circular profile surface for each of the plurality of image capturing units.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

1: Target object
2a and 2b: Circular profile surface
3: Center of circle constituting profile of circular profile surface
4: Rotation axis of target object
5: Circumference of circular profile surface
10: Checking device
20, 20a, 20b, . . . : Electromagnetic wave source
21, 21a, 21b, . . . : Electromagnetic wave
30: Sensor
31, 31a, 31c, and 31d: Electromagnetic wave reception region
31ca through 31ch: Smaller region
31da, 31db, . . . : Image capturing unit

The invention claimed is:

1. A checking device for checking a target object having a circular profile surface, which is a surface whose profile is a circle, while rotating the target object about an axis that passes through a center of the circle and extends in a direction substantially perpendicular to the circular profile surface, said checking device comprising:
at least one electromagnetic wave source which irradiates the circular profile surface of the target object, which is being checked, with an electromagnetic wave; and
an image capturing section which has an electromagnetic wave reception region for receiving the electromagnetic wave which has passed through the target object which is being checked,
in the image capturing section, suitability of portions of the electromagnetic wave reception region for capturing an image of a subject which moves fast being heightened as a distance from the center of the circle increases in a plan view of the circular profile surface of the target object which is being checked.

2. The checking device as set forth in claim 1, wherein:
the electromagnetic wave reception region is divided into a plurality of smaller regions; and
in the plan view of the circular profile surface, the plurality of smaller regions are arranged concentrically with a circumference of the circular profile surface.

3. The checking device as set forth in claim 2, wherein:
the plurality of smaller regions receive the electromagnetic wave, which passes through a certain portion of the circular profile surface, at respectively different points in time; and
said checking device checks presence or absence of a foreign substance adhering to the certain portion by superimposing a plurality of images of the certain portion which have been obtained when the plurality of smaller regions receive the electromagnetic wave.

4. The checking device as set forth in claim 2, wherein:
the at least one electromagnetic wave source of said checking device is a plurality of electromagnetic wave sources which are associated with the respective plurality of smaller regions; and
each of the plurality of electromagnetic wave sources is provided such that a direction from each of the plurality of electromagnetic wave sources to a corresponding one of the plurality of smaller regions is substantially perpendicular to the circular profile surface.

5. The checking device as set forth in claim 1, wherein:
the electromagnetic wave reception region is constituted by a plurality of image capturing units;
the at least one electromagnetic wave source of said checking device is a plurality of electromagnetic wave sources which are associated with the respective plurality of image capturing units; and
each of the plurality of electromagnetic wave sources is provided such that a direction from each of the plurality of electromagnetic wave sources to a corresponding one of the plurality of image capturing units is substantially perpendicular to the circular profile surface.

6. A checking method for checking a target object having a circular profile surface, which is a surface whose profile is a circle, while rotating the target object about an axis that passes through a center of the circle and extends in a direction substantially perpendicular to the circular profile surface, said checking method comprising the steps of:
irradiating the circular profile surface of the target object, which is being checked, with an electromagnetic wave; and
receiving, by an electromagnetic wave reception region included in an image capturing section, the electromagnetic wave which has passed through the target object which is being checked,
in the image capturing section, suitability of portions of the electromagnetic wave reception region for capturing an image of a subject which moves fast being heightened as a distance from the center of the circle increases in a plan view of the circular profile surface of the target object which is being checked.

7. The checking method as set forth in claim 6, wherein:
the electromagnetic wave reception region is divided into a plurality of smaller regions; and
in the plan view of the circular profile surface, the plurality of smaller regions are arranged concentrically with a circumference of the circular profile surface.

8. The checking method as set forth in claim 7, wherein:
the plurality of smaller regions receive the electromagnetic wave, which passes through a certain portion of the circular profile surface, at respectively different points in time; and
in said checking method, presence or absence of a foreign substance adhering to the certain portion is checked by superimposing a plurality of images of the certain portion which have been obtained when the plurality of smaller regions receive the electromagnetic wave.

9. The checking method as set forth in claim 7, wherein the electromagnetic wave is generated in a direction substantially perpendicular to the circular profile surface for each of the plurality of smaller regions.

10. The checking method as set forth in claim 6, wherein:
the electromagnetic wave reception region is constituted by a plurality of image capturing units; and
the electromagnetic wave is generated in a direction substantially perpendicular to the circular profile surface for each of the plurality of image capturing units.

* * * * *